United States Patent [19]
Privitera et al.

[11] Patent Number: 5,591,192
[45] Date of Patent: Jan. 7, 1997

[54] SURGICAL PENETRATION INSTRUMENT INCLUDING AN IMAGING ELEMENT

[75] Inventors: Salvatore Privitera, West Chester; Richard F. Schwemberger; Ron Kolata, both of Cincinnati, all of Ohio

[73] Assignee: Ethicon Endo-Surgery, Inc., Cincinnati, Ohio

[21] Appl. No.: 384,505

[22] Filed: Feb. 1, 1995

[51] Int. Cl.$^6$ ........................................... A61B 1/00
[52] U.S. Cl. ........................... 606/185; 604/164; 600/114
[58] Field of Search ................................ 600/114, 117, 600/104, 129, 160, 137, 138, 165, 176; 606/185, 167; 604/164, 264

[56] References Cited

U.S. PATENT DOCUMENTS 5,364,372  11/1994  Danks et al. ................... 604/184 X
5,441,041  8/1995   Sauer et al. ................... 606/185 X

OTHER PUBLICATIONS

Visiport/Surgiview Optical Entry System, Product Literature, 5 pp., 1994.

*Primary Examiner*—Richard J. Apley
*Assistant Examiner*—Beverly M. Flanagan
*Attorney, Agent, or Firm*—Matthew S. Goodwin

[57] ABSTRACT

A surgical instrument for penetrating bodily tissue including an imaging element providing the capability for simultaneous visualization during penetration is disclosed. A transparent portion of the imaging element extends from the distal end of an elongated, substantially hollow shaft. The imaging element is shaped to enlarge an opening as the instrument is advanced into bodily tissue, and an endoscope can be inserted through the shaft adjacent the imaging element to visualize the penetration of tissue as the instrument is advanced. The imaging element may be substantially hollow, and have an annular interior region inside the shaft distal end. The endoscope can then be positioned to rest on the annular region to prevent glare from the reflection of light traveling from the endoscope to the window surface. The imaging element may also have a blade for facilitating the advance of the instrument through tissue. The blade not only has a sharp, linear cutting edge, but also a blunt edge for preventing inadvertent cutting of tissue. The blunt edge is preferably located near the tip and base of the imaging element. Additionally, the imaging element is generally conical and the penetrating surface has a region extending at an obtuse angle relative to the exterior surface of the conical element, and a second region extending generally parallel to the exterior surface of the conical element.

20 Claims, 6 Drawing Sheets

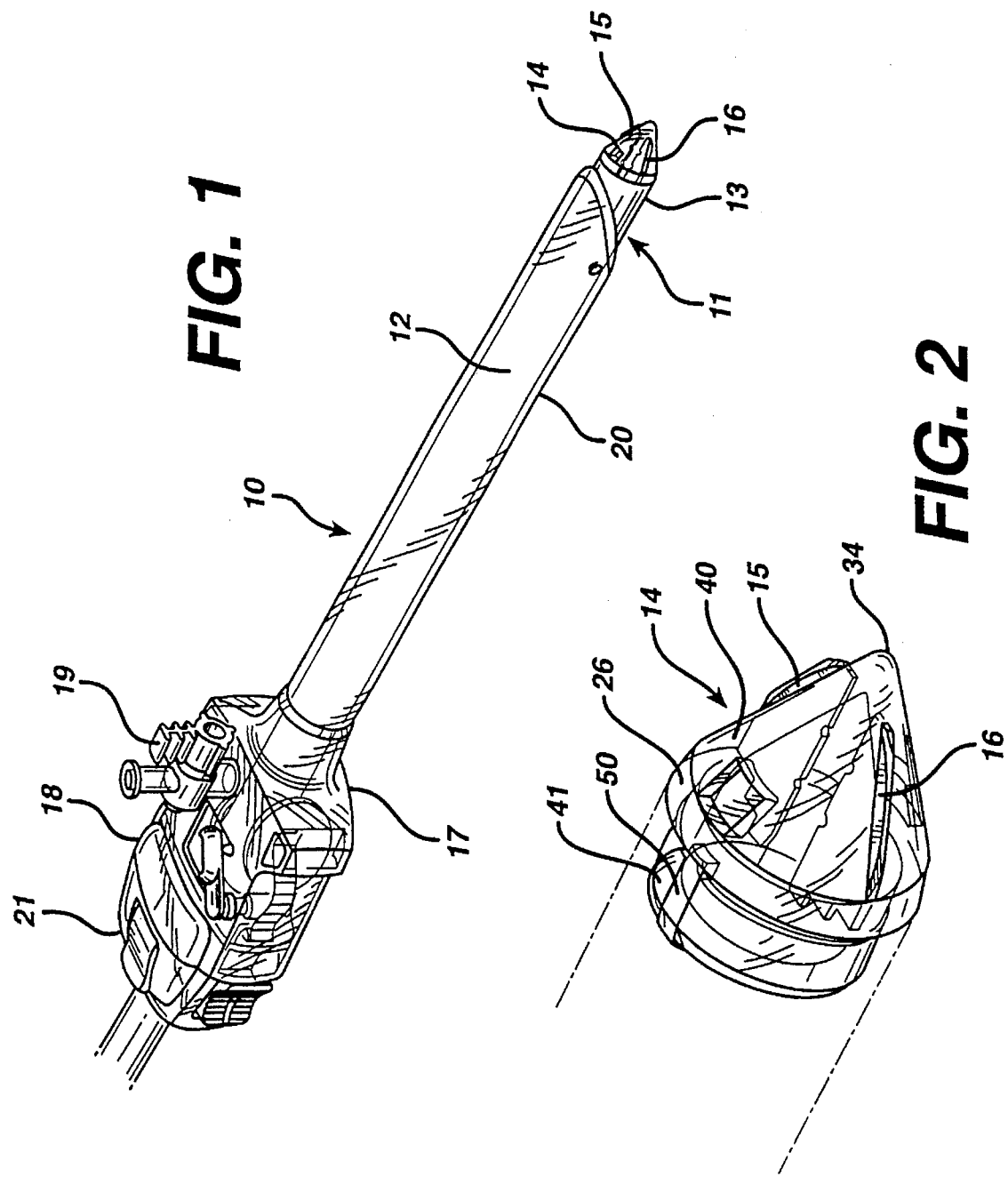

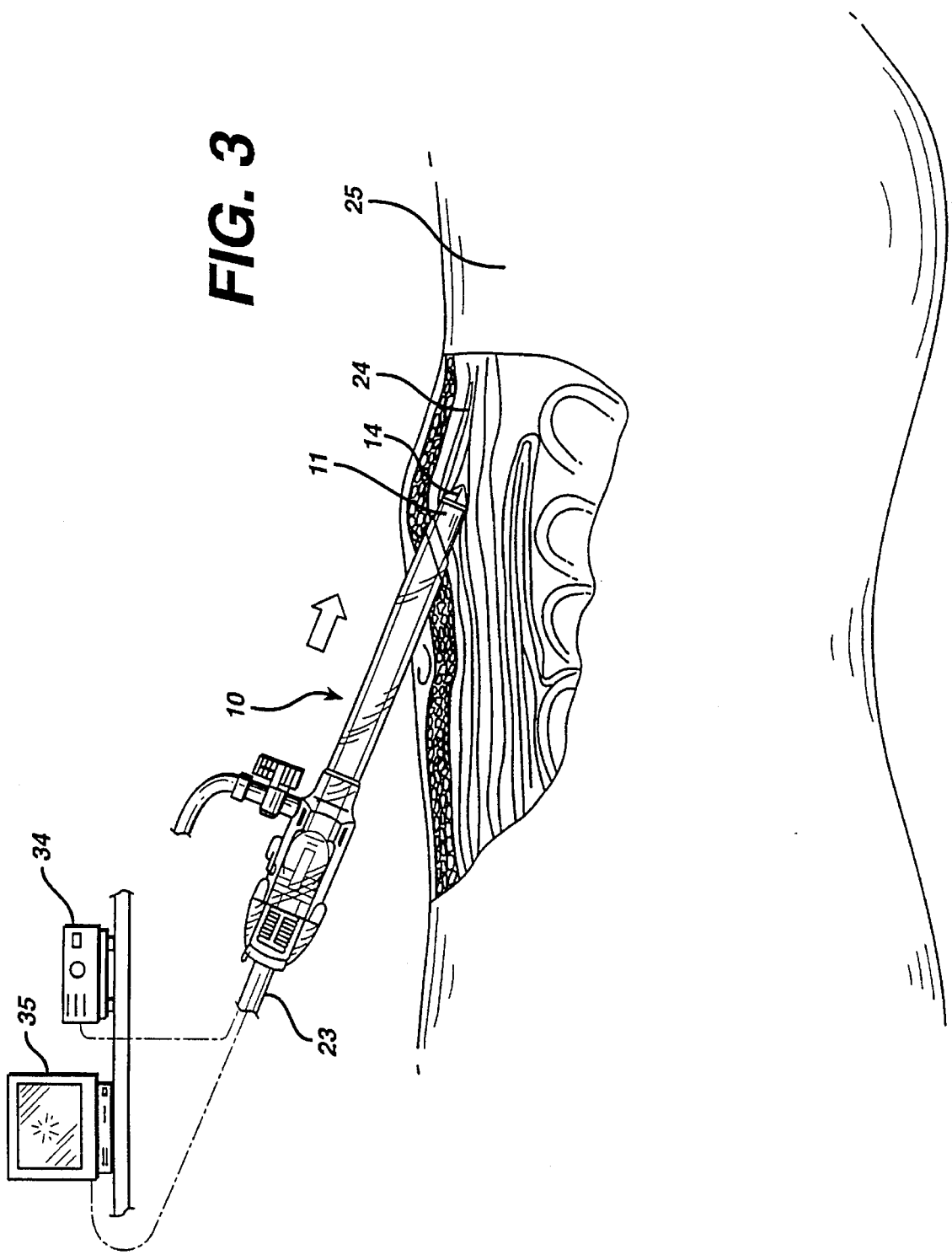

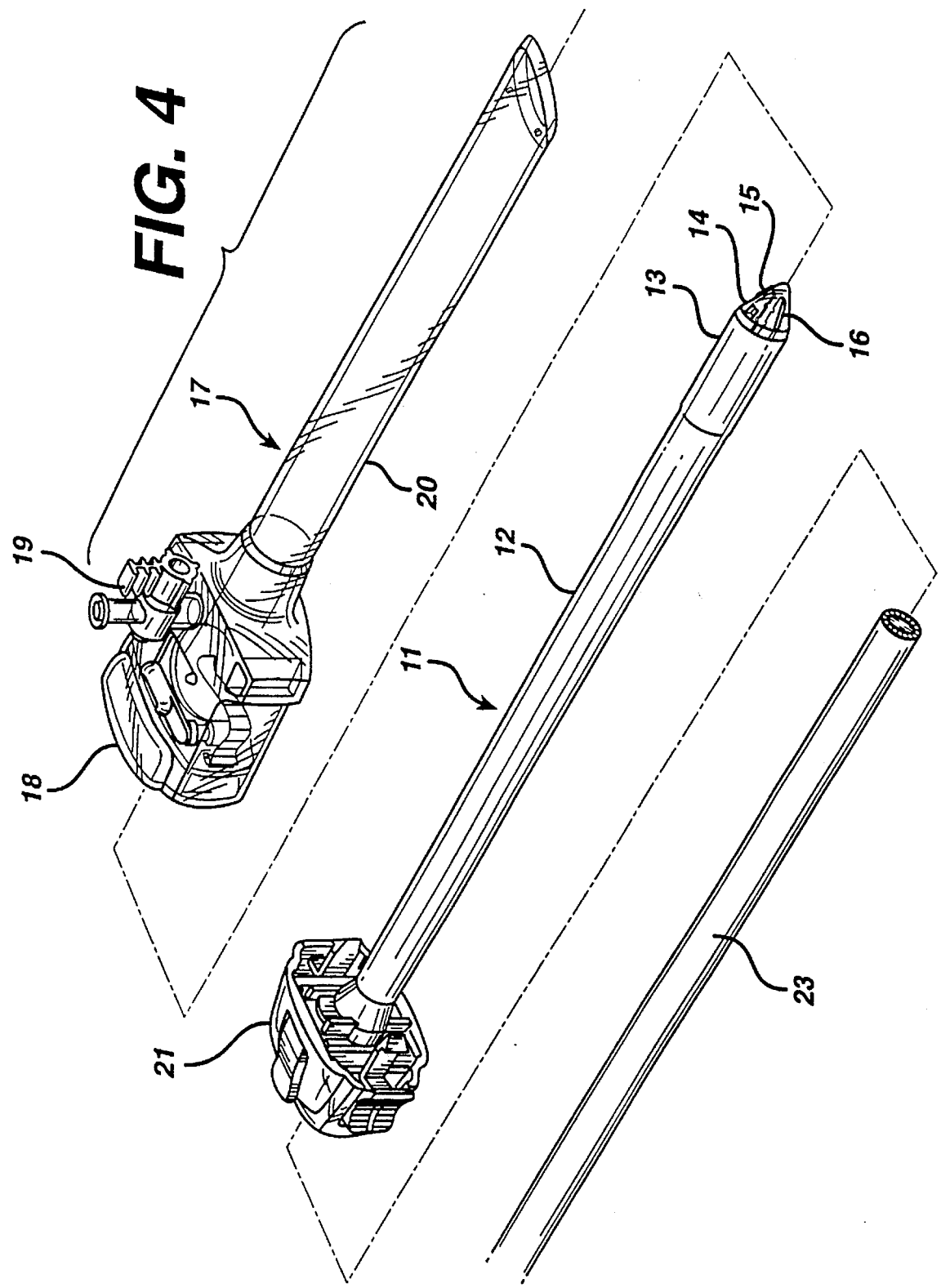

SURGICAL PENETRATION INSTRUMENT INCLUDING AN IMAGING ELEMENT

BACKGROUND OF THE INVENTION

This invention relates to surgical instruments for penetrating or dissecting bodily tissue. More specifically, it relates to penetrating instruments which incorporate an imaging element for viewing. These instruments allow access into a body cavity when the instrument is advanced into the tissue, and simultaneously provide the ability to visualize the penetrated tissue during the advancement.

One of the key surgical activities which is required during every surgical procedure is the creation of an access opening into the body cavity at the desired surgical site. For many years, the surgeon created the access opening by simply making a large incision through the body wall to expose the body cavity. The length of the incision would depend on the size of conventional surgical instruments and the ability of the surgeon to properly and efficiently use these instruments within the body cavity through the incision created. Once the surgeon finished the surgical procedure, the incision could be fastened using known techniques. Unfortunately, due to the nature of these conventional, open surgical procedures, long incisions were often necessary. Open surgery can therefore be traumatic to the patient because, among other things, the recuperative period required to fully heal from the effects of the large incision may be significant.

Since a patient's recuperative period can be significant in connection with conventional open surgery, new surgical procedures and instruments to support those procedures are becoming available. The most popular alternative to open surgery currently is endoscopic surgery. Endoscopic surgery involves the use of a number of small diameter openings providing access into the body cavity. Unlike the large incisions required for open surgery, these small diameter openings readily heal following surgery, and require much less recuperation time for the patient.

The cornerstones which have made endoscopic surgical procedures possible are the miniaturized camera, or endoscope, and the surgical penetration instrument providing the small diameter opening for access into the body cavity, conventionally referred to as the trocar. Since both of these instruments are critical for the performance of endoscopic surgery, each will be discussed briefly below.

An endoscope is an elongated, generally cylindrical imaging and visualization instrument. It can be attached to a light source which provides illumination within the body cavity at the surgical site. The endoscope contains a miniaturized camera lens which is capable of transmitting the illuminated images at the surgical site to the surgeon during a surgical procedure. The endoscope is frequently attached to a video monitor during endoscopic surgery, so that the surgical team can observe the surgical procedure within the body cavity on the video monitor screen. The endoscope has made it possible to indirectly observe the surgical procedure without having the direct access into the body cavity, and consequently the large incisions it requires to create such direct access.

Critical to the success of endoscopic surgery is the creation of a small diameter passageway into the body cavity for subsequent insertion and withdrawal of surgical instruments. These instruments include, for example, an endoscope, and elongated instruments to cut, fasten, coagulate and excise desired tissue. The trocar has become the instrument of choice to create this small diameter passageway. A trocar is a penetrating assembly including a cutting tool, commonly referred to as the trocar obturator. The obturator has an elongated, cylindrical shaft from which extends a penetrating tip to create and enlarge an opening into tissue as the obturator is advanced. The obturator is slidably received in a sleeve, commonly referred to as the trocar cannula. As the obturator is advanced into the tissue, the cannula likewise is advanced. When the obturator has completely punctured the body wall, the obturator is withdrawn from the trocar assembly, leaving behind the trocar cannula. The trocar cannula then provides the passageway into the body cavity through a relatively small diameter opening.

One of the first technical challenges in connection with the design and manufacture of the trocar related to the incorporation of features into the trocar to enhance its safety. Specifically, it was important to develop a safety trocar which could substantially lessen the possibility of unintentional tissue or organ puncture. The seminal patent that describes a mechanism for protecting bodily tissue and organs from inadvertent puncture during advancement of the instrument into the body cavity is U.S. Pat. No. 4,535,773 (Yoon, issued August, 1985). This patent describes a trocar assembly which includes a safety shield interposed between the trocar obturator and cannula. The shield is biased in an extended position to cover the penetrating tip of the obturator. When the surgeon desires to penetrate tissue with the trocar, the safety shield retracts and exposes the penetrating tip when the surgeon applies pressure against the body wall. The shield remains in the retracted position so long as pressure is continuously applied. When the surgeon fully punctures the body wall, the pressure is relieved and the safety shield returns to its extended position covering the penetrating tip. Therefore, inadvertent puncture of bodily tissue and organs within the body cavity can be avoided. Another trocar assembly with a safety shield mechanism is described in U.S. Pat. No. 5,226,426 (Yoon, issued Jul. 13, 1993). This patent describes a trocar obturator in the form of a hollow needle through which the safety shield (or safety "probe"), is disposed. Once again, the safety probe covers the sharp tip of the needle until pressure is applied during insertion.

Since the development of the safety-shielded trocar, other mechanisms for protecting tissues and organs from inadvertent puncture during endoscopic surgery have been developed. For example, mechanisms have been developed where the obturator retracts into the trocar cannula after puncture. These "retractable obturator" trocars may be equipped with a safety shield which simultaneously moves to an extended position as the obturator retracts within the trocar cannula.

While numerous trocar assemblies have been designed to prevent inadvertent puncture, all of these instruments still have one basic problem. Regardless of the safety mechanisms built into these instruments, the surgeon cannot avoid the fact that he is still puncturing tissue blindly. Not only is the puncture performed blindly, but the instruments are expensive to manufacture and occasionally fail in connection with the safety features incorporated to prevent inadvertent puncture during the blind insertion. Therefore, significant new designs for trocar assemblies have been developed.

One of the more remarkable developments in the design of trocar assemblies relates to the incorporation of visualization concurrently with penetration. This has been made possible by the "marriage" of the endoscope for imaging and visualization, and the trocar for penetration to provide the endoscopic access opening. The first patent to describe a surgical penetration instrument adapted for visualization during penetration is U.S. Pat. No. 5,271,380 (Riek, et al., issued Dec. 21, 1993). The Riek patent describes a penetrating instrument including a hollow, cylindrical sleeve and an imaging element attached to the sleeve at its distal end. The imaging element is a transparent, optical "window". In a preferred embodiment, it has a conical configuration to facilitate the advance of the instrument into body tissue. A fiber optic cable extends through the hollow shaft and is positioned adjacent the proximal end of the window. It delivers light from a light source through the optical window into surrounding bodily tissue. A camera lens is also provided in the shaft to deliver illuminated images transmitted through the optical window to the surgeon. When the surgeon advances the instrument into bodily tissue, the surgeon can view the tissue in front of and surrounding the optical window during the penetration. This feature is significant because the surgeon can adjust the path of advancement if he approaches tissue or organs which should not be touched. In this way, the incorporation of a safety shield or another mechanism to protect tissue or organs from inadvertent puncture during a blind insertion is unnecessary.

Although the surgical penetration instrument described in the Riek patent represents a major advance in trocar technology, the clarity of images transmitted to the surgeon of the surrounding tissue during advancement is less than what would be optimally desired. Significantly, the transparent optical window is hollow, and the fiber optic cable delivering light into the surrounding tissue for illumination is spaced from the window surface. Light rays must therefore travel from the cable through the void of the hollow window before contacting the window surface. As light is carried from the fiber optic cable to the surface of the window, a significant proportion of that light will not pass through the window into the surrounding tissue, but rather reflect back into the camera lens. This reflection causes unwanted glare, and prevents optimum clarity during visualization.

In another embodiment, the Riek patent describes a second fiber optic cable for delivering light which extends through the window and is positioned at the tip of the window. While this cable does indeed contact the surface of the window, it only does so at the tip and therefore is unable to provide adequate illumination of the tissue surrounding the entire conical window. In other words, it can only provide illumination of tissue in front of the tip of the window.

Another recently issued patent representing yet another significant advance in the state of the art with respect to surgical penetration instruments providing simultaneous visualization is U.S. Pat. No. 5,334,150 (Kaali, issued Aug. 2, 1994). The Kaali patent also describes an instrument including an elongated hollow shaft to which is attached an imaging element in the preferred form of a transparent conical window. However, instead of extending a fiber optic cable and lens into fixed positions adjacent the proximal end of the transparent window within the hollow shaft, the Kaali patent describes using a fully integrated endoscope which can be inserted through the hollow shaft adjacent the window to provide illumination and visualization of tissue in front of and surrounding the transparent window during insertion. Unfortunately, once again the optical clarity of the surrounding tissue as the instrument is advanced is less than ideal. This is so because the transparent window in the specific embodiments illustrated in this patent are substantially solid. Depending on the material of construction for the window, visual distortion and other undesirable optical effects can occur when light travels through the solid mass of the window, Another feature which has recently been added to the surgical penetration instruments described in the Riek and Kaali patents is a cutting blade extending outwardly from the transparent optical window to facilitate the advance of the instrument into tissue. Unfortunately, these blades may inadvertently cut unwanted tissues or organs and cause undesirable damage to gaskets and other delicate elements located within the housing of the cannula sleeve when the instrument is removed from the cannula sleeve.

It should now be apparent to the reader that while significant advances have been made in the development of surgical penetrating instruments adapted for simultaneous visualization, there are still certain problems which need to be overcome. For example, what is needed is a surgical penetration instrument which can provide visualization with the optimum degree of clarity. Additionally, such an instrument would desirably incorporate a blade outwardly of the transparent optical window which would not cause unintended trauma to tissue or damage delicate elements in the cannula housing of the instrument, but rather facilitate the advance of the instrument into tissue for ease of penetration.

SUMMARY OF THE INVENTION

In one aspect of the invention, the invention is an imaging element for a surgical penetration instrument. The instrument has an elongated, generally cylindrical shaft having a distal end and a shaft diameter. The shaft has a lumen through it for receiving an endoscope. The imaging element is attached at the distal end of the shaft. The imaging element is substantially hollow and comprises a generally circular base adjacent the distal end of the shaft. An exterior region extends distally from the base and has a surface configuration shaped to enlarge an opening as the instrument is advanced into bodily tissue. At least a portion of the exterior region is transparent. An annular interior region descends proximally from the base, and the interior region has an annulus diameter less than the base diameter. The interior region descends interiorly into the lumen of the distal end of the shaft.

The imaging element for the surgical penetration instrument of this invention incorporates an annular interior region within the distal end of the shaft. Significantly, when an endoscope is inserted through the lumen of the shaft to the shaft distal end, the periphery of the distal end of the endoscope can rest on the edge surface of the annular interior region of the imaging element. Therefore, the endoscope is not spaced from the surface of the imaging element. The light from the endoscope, which is emitted from the periphery of the distal end of the endoscope, will travel directly from the endoscope into the imaging element and exit the transparent portion of the exterior region of the imaging element to illuminate surrounding tissue as the instrument is advanced. Significantly, light received at the transparent portion of the exterior region does not travel through the void in the hollow window. Reflection of light is therefore avoided without a need to fabricate a solid window. Glare is substantially lessened or eliminated. In so doing, optimum optical clarity is achieved.

In another aspect of the invention, the invention is an imaging element for a surgical penetration instrument. The instrument has an elongated shaft having a distal end. The imaging element is attached at the distal end of the shaft and extends distally from the distal end of the shaft to a tip. At least a portion of the imaging element is transparent and has an exterior surface shaped to enlarge an opening as an instrument is advanced into bodily tissue. The imaging element comprises a blade at the imaging element having a tissue contacting portion outwardly of the element. The blade extends from adjacent the distal end of the shaft toward the tip, and the tissue contacting portion of the blade has two sidewalls converging to a penetrating surface. The penetrating surface has first and second sections, in which the first section has a blunt edge surface extending from the exterior surface of the imaging element to the second section. The second section has a sharp, linear edge surface.

The incorporation of a blunt edge surface onto the penetrating surface of the blade dramatically reduces the risk of inadvertent cutting of tissue or organs as the instrument is advanced. Likewise, when the instrument is used with a cannula sleeve, it also dramatically reduces the risk of cutting gaskets, seals and other elements residing within the housing of the cannula sleeve during insertion and withdrawal from the sleeve. Instead, the blade, as it is particularly set forth in this invention, facilitates the enlargement of an opening as the instrument is advanced without inadvertently cutting or tearing the tissue during such advancement.

In yet another aspect of this invention, the invention is an imaging element for a surgical penetration instrument. The instrument has an elongated shaft having a distal end. The imaging element is attached at the distal end of the shaft and extends distally from the distal end of the shaft to a tip. At least a portion of the imaging element is transparent and has a generally conical exterior surface. The imaging element comprises a blade at the imaging element having a tissue-contacting portion outwardly of the element. The blade extends from adjacent the distal end of the shaft toward the tip, and the tissue-contacting portion of the blade has two side walls converging to a penetrating surface. The penetrating surface has first and second sections. The first section extends from the exterior surface of the imaging element adjacent the shaft distal end to the second section, and is displayed at an obtuse angle relative to the exterior surface. The second section is generally parallel to the exterior surface.

The angular relationship between the exterior surface of the imaging element and the first section of the penetrating surface of the blade provides a smooth transition to the second section of the penetrating surface. The smooth transition facilitates the gradual enlargement of an opening as the instrument is advanced into tissue or prevents inadvertent cutting or tearing of that tissue during such advancement. Significantly, this blade design can eliminate the need for a squared-off or sharp corner on the tissue-contacting portion of the blade. When a sharp corner can be eliminated, the risk of inadvertently cutting or tearing tissue as the instrument is advanced is substantially reduced. Likewise, damage to gaskets and seals when the instrument is inserted or withdrawn from a cannula sleeve can also be reduced.

In a further aspect of this invention, the invention is an imaging element for a surgical penetration instrument. The instrument has an elongated shaft and a distal end. The imaging element is attached at the distal end of the shaft and extends distally from the distal end of the shaft to a tip. At least a portion of the imaging element is transparent and has a generally conical exterior surface. The imaging element comprises a blade at the imaging element having a tissue-contacting portion outwardly of the element. The blade extends from adjacent the distal end of the shaft toward the tip, and the tissue-contacting portion of the blade has two sidewalls converging to a penetrating surface. The penetrating surface has first, second and third sections. The second section is interposed between the first and second sections, and is generally parallel to the exterior surface of the imaging element. The first section extends from the exterior surface of the imaging element adjacent the shaft distal end to the second section. The third section extends from the exterior surface of the imaging element at a position adjacent to or proximal of the tip of the imaging element to the second section. Significantly, the third section has a generally rounded corner.

The generally rounded corner displayed on the third section of the penetrating surface of the blade is another way to provide a smooth transition through the tissue as the penetrating surface of the blade is advanced, in contrast to a blade having a squared-off corner. The smooth transition promotes less traumatic penetration or dissection of tissue as the instrument is advanced distally. An opening is gradually enlarged as the tissue contacts the rounded corner of the blade. Therefore, inadvertent cutting or tearing of that tissue can be avoided.

The surgical penetration instrument of this invention is ideally suited for all applications for which conventional trocars are used. These applications include, but are not limited to, various forms of endoscopic surgery, including laparoscopic and thoracoscopic surgery. It is also envisioned that the surgical penetration instrument of this invention may be used for arthroscopic surgery as well. In addition to those procedures where penetration and puncture of the body wall to provide a passageway for additional endoscopic surgical instrumentation is desired, it is also anticipated that this instrument may be used in procedures not requiring complete penetration and puncture through the body wall. For example, certain procedures require a penetrating or dissecting instrument to tunnel through layers of tissue without breaking certain other layers of tissue. Emerging procedures in connection with laparoscopic hernia repair and saphenous vein harvesting for cardiovascular surgery incorporate tunneling techniques to provide access to a desired surgical site remote from the point of entry. The surgical user may well find the surgical penetration instrument of this invention, which offers the dual capabilities of dissection and visualization, to be particularly well suited for these emerging procedures. Finally, the reader must also realize that although this instrument is particularly adapted for endoscopic surgical applications, it may also find use for a wealth of applications in conventional open surgery.

BRIEF DESCRIPTION OF THE DRAWINGS

FIG. 1 is a perspective view of an assembly including the surgical penetration instrument with the imaging element of the present invention.

FIG. 2 is an enlarged perspective view of the imaging element of the instrument.

FIG. 3 is a side elevational view and partial cross-section of the assembly including the instrument shown in the process of penetrating bodily tissue in a surgical patient.

FIG. 4 is an exploded perspective view of the assembly including the surgical penetration instrument with the imaging element.

DETAILED DESCRIPTION OF THE PREFERRED EMBODIMENT

Figure 5:
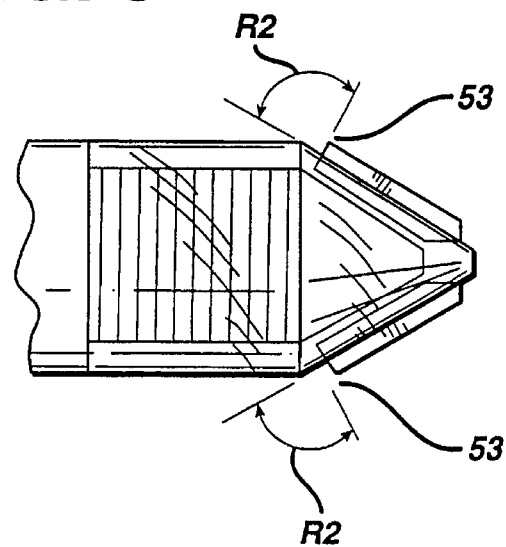
FIG. 5 is a top plan view of an imaging element of the prior art.

Reference numerals are used in this description to designate the various components and elements of the surgical penetration instrument of this invention. Identical reference numerals designated in the various drawings refer to the identical element or component of the surgical penetration instrument. As used in this description, "proximal" or "proximally" refers to that portion of the instrument, component or element which extends toward the user. Conversely, "distal" or "distally" refers to that portion of the instrument, component or element which extends away from the user.

Referring now to FIGS. 1, 2 and 4, there is a shown an assembly 10 which incorporates a surgical penetration instrument having the imaging element which is the subject of the claimed invention. The surgical penetration instrument 11 has a cylindrical, elongated hollow shaft 12. The hollow shaft is sized for receiving a conventional endoscope. The shaft has a distal end 13 from which extends a portion of the imaging element 14. The imaging element is hollow and entirely transparent, and is ideally a one-piece construction. In other words, it is advantageously composed of a single piece of material, such as a plastic or a glass. Facilitating the penetration of imaging element 14 as instrument 11 is advanced into tissue are first and second blades 15 and 16, respectively, extending outwardly from the transparent imaging element.

The assembly includes a conventional cannula 17. The cannula has a cannula housing 18 and stopcock 19. Extending distally from the cannula housing 18 is the cannula sleeve 20. The surgical penetration instrument 11 is inserted into and through the cannula housing 18 and sleeve 20. The transparent imaging element 14 of the instrument, and a portion of the shaft distal end 13 of the instrument, extend distally from the cannula sleeve 20.

The surgical penetration instrument 11 has at its proximal end an instrument hub 21. The hub can be attached to the cannula housing 18 when the instrument is inserted into and through the cannula housing and sleeve. If desired, a pressurizing fluid such as carbon dioxide can be selectively pumped through the cannula sleeve 20 via stopcock 19 into the body of the patient.

The assembly illustrated in FIG. 1, and in particular the surgical penetration instrument 11 including the transparent imaging element 14 of this invention, can be used to penetrate or dissect tissue while providing simultaneous visualization as the tissue is penetrated or dissected. As illustrated in FIG. 3, the assembly 10 is advanced in the direction illustrated by the arrow through bodily tissue 24 of a surgical patient 25. A conventional endoscope 23 can be inserted through the hollow shaft 12 of instrument 11 so that the endoscope is positioned adjacent the proximal end of transparent imaging element 14. The endoscope 23 is connected to a light source 34 to provide illumination through the transparent penetrating tip 14 to the surgical site. It is also connected to a video monitor 35 to display the illuminated images transmitted from the surgical site. In this way, the user can readily monitor the advance of instrument 11 through bodily tissue 24 from video monitor 35.

When the advancement of the surgical penetration instrument 11 is completed, the instrument and the endoscope 23 may be removed from cannula 17 of assembly 10, so that additional instrumentation can then be inserted through the cannula to the surgical site to complete a desired surgical procedure.

Figure 7:
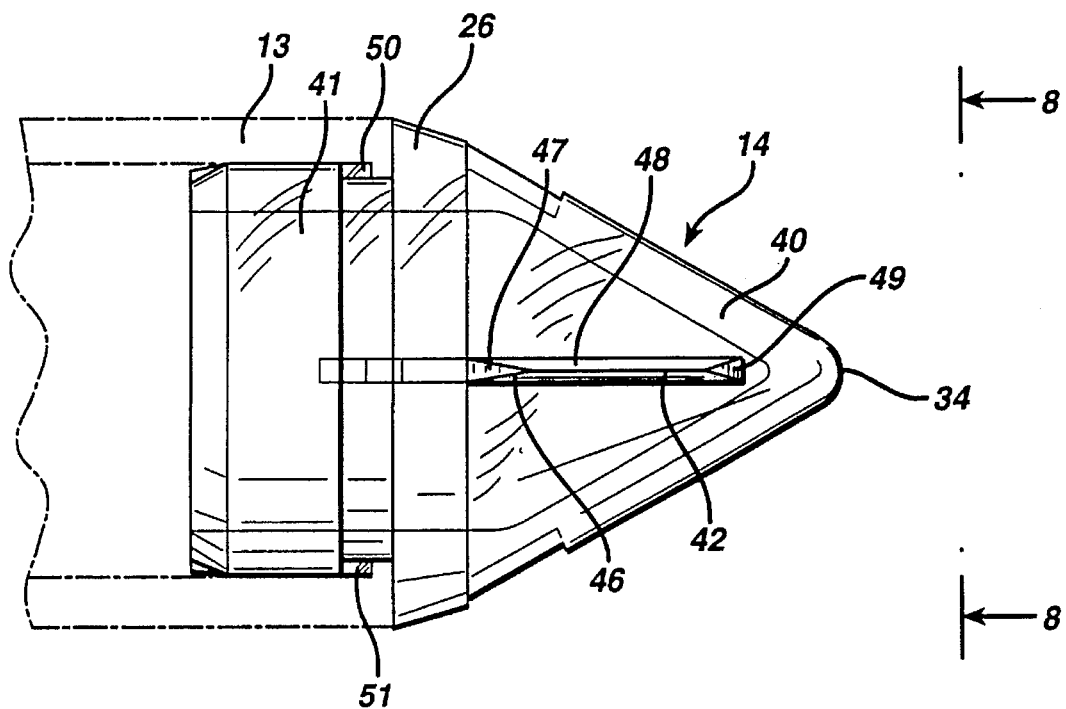
FIG. 7 is a side elevational view of the imaging element.
Figure 8:
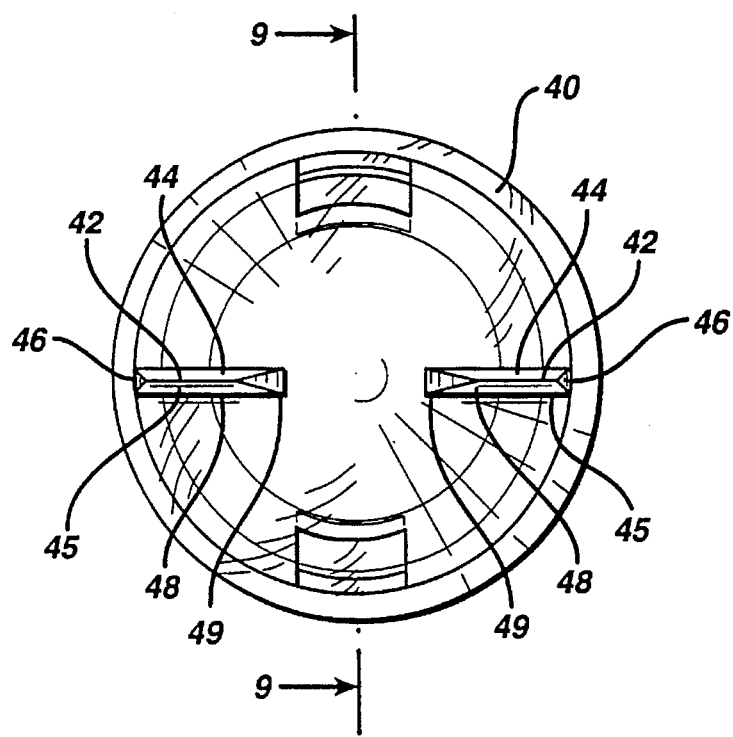
FIG. 8 is an end elevational view of the distal tip of the imaging element as seen along view line 8—8 of FIG. 7.

Referring now to FIGS. 2 and 7, the transparent conical imaging element 14 of this invention has a circular base 26 adjacent the shaft distal end 13. An entirely transparent conical exterior region 40 having a generally tapering configuration in the form of a right circular cone, extends distally from the circular base to a blunt point 34. Since the exterior region is entirely transparent, the transparent portion of the exterior region extends through substantially 360°. An annular interior region 41 having a diameter less than the diameter of circular base 26 descends proximally from the base into the lumen of the distal end of the shaft. The annular interior region 41 is generally in the form of a cylinder which has an outer wall diameter sized to frictionally contact the shaft distal end 13. The annular interior region includes first and second longitudinally extending ribs 50 and 51 spaced about 180° apart. These ribs help to secure and seal the imaging element 14 to the shaft distal end 13.

Figure 9:
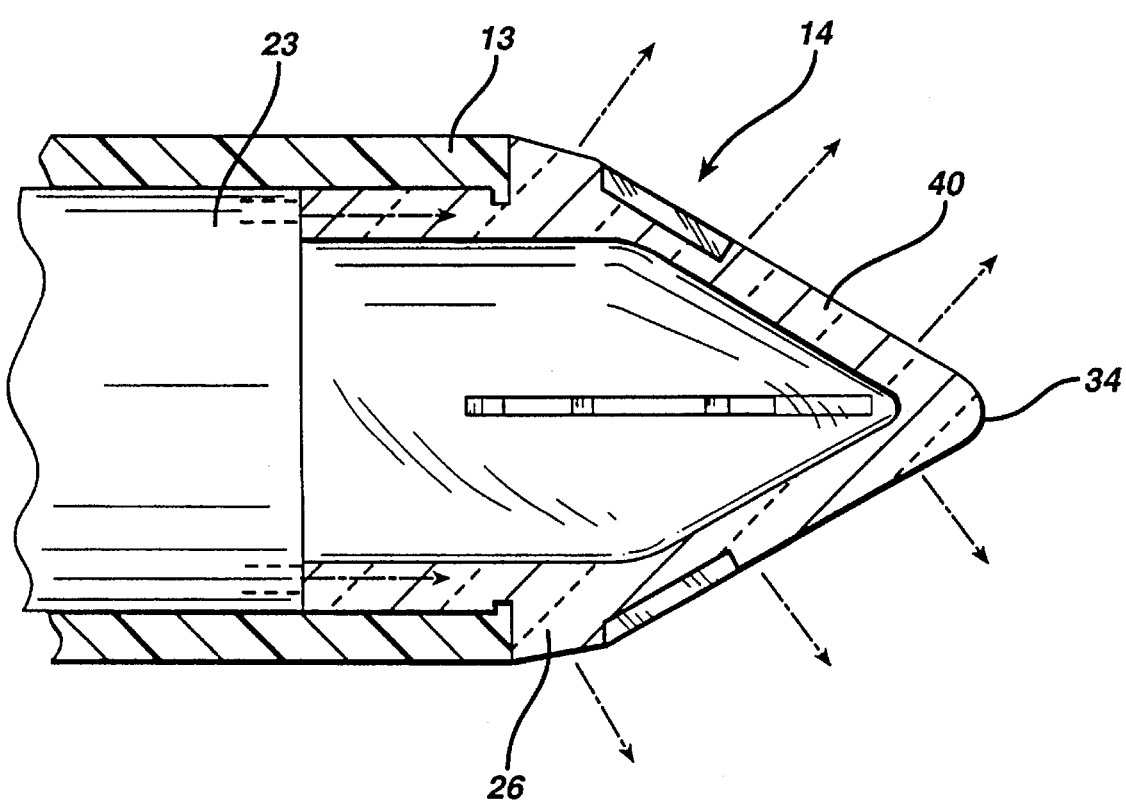
FIG. 9 is a side cross-sectional view of the imaging element indicating the path of light transmission when the distal end of an endoscope abuts the imaging element.

Accordingly, as best shown in FIG. 9, when endoscope 23 is received into the lumen of hollow shaft 12 and extends to the shaft distal end 13, the periphery of the endoscope abuts the annular interior region 41 of the transparent imaging element 14. Consequently, light rays emitted from the endoscope 23, which are emitted from the periphery of the endoscope, are delivered directly into and through the wall thickness of the hollow imaging element 14 into the surgical site. The pathway of the light rays emitted from endoscope 23 is shown generally by the arrows displayed in FIG. 9.

Referring to FIGS. 2, 6, 7 and 8, first and second blades 15 and 16 each have a tissue contacting portion 42 extending outwardly from the conical exterior region 40 of the transparent imaging element 14. The tissue contacting portion of each blade includes first and second sidewalls 44 and 45, respectively, which converge to form a penetrating surface 46. The penetrating surface is a continuous surface, and includes first, second and third sections 47, 48 and 49, respectively. The first section extends from adjacent the circular base 26 to the second section 48. The first section 47 has a blunt arcuate edge surface. The second section 48 extends from the first section to the third section 49. The second section has a relatively sharp, linear edge surface. Finally, the third section 49 extends from the second section to adjacent the conical exterior region 40 of the imaging element 14 at a position proximal of the tip 34 of the imaging element. Similarly to the surface characteristic of the first section, the third section has a blunt arcuate edge surface.

First and second blades 15 and 16 are straight blades spaced approximately 180° from each other. The blades extend longitudinally in a plane parallel to the longitudinal-axis of the hollow shaft 12 and conical imaging element 14.

Figure 6:
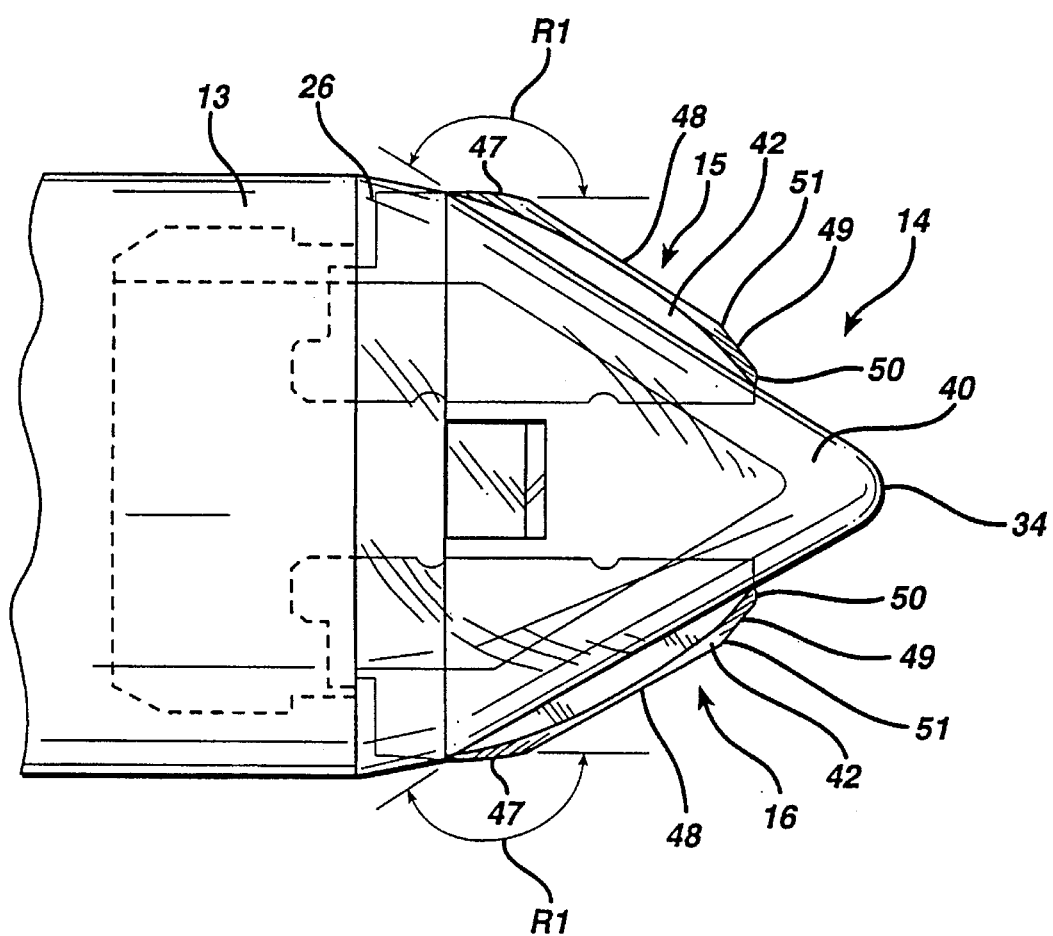
FIG. 6 is an enlarged top plan view of the imaging element of the present invention.

Other aspects of the design of the blade configuration for the first and second blades 15 and 16 are illustrated in FIG. 6. The first section 47 of each of the penetrating surfaces of the first and second blades extends distally from circular base 26 at an obtuse angle designated as R1 in relation to the surface line of the conical exterior region 40 of imaging element 14. The second sections 48 of the penetrating surfaces for each of the blades extends generally parallel to the surface of the conical exterior region 40. In addition, the third section 49 of the penetrating surfaces of the blades has a first rounded corner 50 adjacent the surface of the conical exterior region 40, and a second rounded corner 51 spaced from first rounded corner 50 and adjacent to the second section 48.

In contrast, the prior art blade configuration, which is illustrated in FIG. 5, has a squared-off proximal corner 53 adjacent the distal end of the shaft. Unlike the obtuse angle generated in connection with first section 46 of the penetrating surface of the imaging element 14 illustrated in FIG. 6, the corresponding angle R2 generated in FIG. 5 is approximately 90°. Additionally, the prior art blade configuration also includes a squared-off distal corner 52.

The reader should realize that this detailed description of the most preferred embodiment of the surgical penetration instrument, including the imaging element of this invention, does not preclude numerous additional embodiments which are not particularly illustrated in the drawings, but nevertheless fall within the scope of the appended claims. In other words, it is the appended claims which define the scope of the invention, and not this detailed description. One skilled in the art can readily envision numerous additional embodiments which fall within the scope of the appended claims. For example, the claimed invention should in no way be construed to be limited to an imaging element for a surgical penetration instrument requiring the incorporation of blades or a particular blade configuration. It may be desirable for certain embodiments to eliminate one or more of the blades because less traumatic advancement is desired. Alternatively, if blades are incorporated onto the imaging element, the invention should not be construed to limit the blade configuration to two straight blades. More than two blades can extend from the imaging element, or for that matter, only one blade may extend from the element and still be within the scope of the claimed invention. Similarly, the blade or blades need not be straight, but rather blades may be helical in form, or some other configuration.

What is claimed is:

1. An imaging element adapted for use with a surgical penetration instrument, said instrument having an elongated, generally cylindrical shaft having a distal end and a shaft diameter, said shaft having a lumen therethrough for receiving an endoscope to deliver light for illumination of a body cavity and to transmit an illuminated image from said body cavity through a camera lens of said endoscope, said imaging element attached at said shaft distal end;

wherein said imaging element is hollow and comprises a generally circular base adjacent said shaft distal end, said base having a base diameter substantially the same as said shaft diameter; an exterior region extending distally from said base and having a surface configuration shaped to enlarge an opening as said instrument is advanced into bodily tissue, at least a portion of said exterior region being transparent; and an annular interior region descending proximally from said base, said annular interior region having an annulus diameter less than said base diameter, said annular interior region descending interiorly into said lumen of said shaft distal end;

wherein when said endoscope is received in said lumen of said shaft, said endoscope abuts said annular interior region of said imaging element, said light delivered from said endoscope for illumination of said body cavity is emitted directly into said hollow imaging element so as to avoid reflecting said light into said camera lens of said endoscope to lessen unwanted glare on said illuminated image.

2. The imaging element of claim 1 wherein said exterior region has a generally tapering configuration extending distally from said base.

3. The imaging element of claim 2 wherein said exterior region is generally conical.

4. The imaging element of claim 3 wherein said exterior region is in the form of a right circular cone.

5. The imaging element of claim 4 wherein said transparent portion of said exterior region extends through substantially 360°.

6. The imaging element of claim 5 wherein said exterior region is entirely transparent.

7. The imaging element of claim 6 wherein said imaging element is an integral, one-piece element.

8. The imaging element of claim 7 wherein said imaging element is entirely transparent.

9. The imaging element of claim 8 wherein said imaging element further comprises a cutting element at said exterior region for facilitating the advance of said instrument into bodily tissue.

10. The imaging element of claim 9 wherein said cutting element is a blade having a sharp, linear edge.

11. An imaging element adapted for use with a surgical penetrating instrument, said instrument having an elongated shaft having a distal end, said imaging element attached at said shaft distal end and extending distally therefrom to a tip, at least a portion of said imaging element being transparent and having a generally conical exterior surface;

wherein said imaging element comprises a blade at said imaging element having a tissue contacting portion outwardly of said element, said blade extending from adjacent said shaft distal end toward said tip, said tissue contacting portion of said blade having two sidewalls converging to a penetrating surface, said penetrating surface having first and second sections, wherein said first section extends from said exterior surface adjacent said shaft distal end to said second section, said first section is displayed at an obtuse angle relative to said exterior surface, and said second section is generally parallel to said exterior surface.

12. The imaging element of claim 11 wherein said penetrating surface includes a third section extending from a position proximal of or adjacent to said tip of said imaging element to said second section, and said second section is interposed between said first and third sections.

13. The imaging element of claim 12 wherein said third section has a generally rounded first corner.

14. The imaging element of claim 13 wherein said third section has a generally rounded second corner spaced from said first corner.

15. The imaging element of claim 14 wherein said blade is a generally straight blade extending longitudinally.

16. The imaging element of claim 15 wherein said imaging element is a transparent conical element, and said conical element is in the form of a right circular cone.

17. An imaging element adapted for use with a surgical penetrating instrument, said instrument having an elongated shaft having a distal end, said imaging element attached at said shaft distal end and extending distally therefrom to a tip, at least a portion of said imaging element being transparent and having a generally conical exterior surface;

wherein said imaging element comprises a blade at said imaging element having a tissue-contacting portion outwardly of said element, said blade extending from adjacent said shaft distal end toward said tip, said tissue contacting portion of said blade having two sidewalls converging to a penetrating surface, said penetrating surface having first, second and third sections, wherein said second section is interposed between said first and third sections, and is generally parallel to said exterior surface of said imaging element, said first section extends from said exterior surface adjacent said shaft distal end to said second section at an obtuse angle relative to said exterior surface, and said third section extends from a position proximal of or adjacent to said tip to said second section, and said third section has a generally rounded first corner.

18. The imaging element of claim 17 wherein said third section has a generally rounded second corner spaced from said first corner.

19. The imaging element of claim 18 wherein said blade is a generally straight blade extending longitudinally.

20. The imaging element of claim 19 wherein said imaging element is a transparent conical element, and said conical element is in the form of a right circular cone.

* * * * *